United States Patent [19]

Sandel

[11] Patent Number: 5,469,600
[45] Date of Patent: Nov. 28, 1995

[54] DISPOSABLE COVER FOR CONTOURED SURGICAL LIGHT HANDLE

[75] Inventor: Dan Sandel, Tarzana, Calif.

[73] Assignee: Devon Industries, Inc., Chatsworth, Calif.

[21] Appl. No.: 165,980

[22] Filed: Dec. 13, 1993

Related U.S. Application Data

[63] Continuation-in-part of Ser. No. 902,942, Jun. 23, 1992, abandoned.

[51] Int. Cl.⁶ .............................. B25G 1/02; F21L 15/12
[52] U.S. Cl. .................... 16/111 R; 16/114 R; 362/399
[58] Field of Search ................... D26/113, 140; 16/111 R, 114 R, DIG. 24; 150/155; 206/223, 438; 362/109, 399, 804

[56] References Cited

U.S. PATENT DOCUMENTS

| | | | |
|---|---|---|---|
| D. 279,611 | 7/1985 | Peeler et al. . | |
| D. 289,206 | 4/1987 | Scoville, Jr. et al. | D26/113 |
| D. 300,950 | 5/1989 | Richard . | |
| D. 313,670 | 1/1991 | Barron et al. | D26/113 |
| D. 316,611 | 4/1991 | Spina | D26/113 |
| 2,731,056 | 1/1956 | Anson . | |
| 2,798,938 | 7/1957 | Jewell . | |
| 3,072,955 | 1/1963 | Mitchell | 16/114 R |
| 3,995,856 | 12/1976 | Hollendorfer, Jr. . | |
| 4,135,231 | 1/1979 | Fisher | 362/269 |
| 4,316,237 | 2/1982 | Yamada et al. | 362/33 |
| 4,376,536 | 3/1983 | Martin . | |
| 4,416,166 | 11/1983 | Jannard et al. . | |
| 4,514,995 | 5/1985 | Curtis et al. . | |
| 4,559,671 | 12/1985 | Andrews et al. | 16/111 R |
| 4,605,124 | 8/1986 | Sandel et al. | 206/223 |
| 4,777,574 | 10/1988 | Eisner | 362/399 |
| 4,878,156 | 10/1989 | Hallings et al. | 362/399 |
| 4,921,028 | 5/1990 | Schwartz | 150/155 |
| 4,928,211 | 5/1990 | Hallings et al. | 362/33 |
| 4,937,715 | 6/1990 | O'Shea et al. | 362/268 |
| 4,975,826 | 12/1990 | Bell | 362/376 |
| 4,976,299 | 12/1990 | Bickelman . | |
| 4,994,945 | 2/1991 | O'Shea et al. | 362/268 |
| 5,016,148 | 5/1991 | Kohm | 16/114 R |
| 5,036,446 | 7/1991 | Quintanilla et al. | 362/399 |
| 5,065,296 | 11/1991 | Cude | 16/114 R |
| 5,065,879 | 1/1991 | King | 220/739 |
| 5,156,456 | 10/1992 | Hoftman et al. | 16/114 R |
| 5,165,143 | 11/1992 | Detchon . | |
| 5,193,246 | 3/1993 | Huang | 16/114 R |
| 5,273,157 | 12/1993 | Spina | 16/114 R |
| B1 4,844,252 | 7/1989 | Barron et al. | 206/223 |

FOREIGN PATENT DOCUMENTS

| | | | |
|---|---|---|---|
| 0498950 | 1/1954 | Canada | 150/155 |
| 8907900 | 9/1989 | WIPO . | |

Primary Examiner—Jimmy G. Foster
Attorney, Agent, or Firm—Poms, Smith, Lande & Rose

[57] ABSTRACT

A disposable sterile cover for a contoured handle of a surgical lighting fixture, which is formed from a thin-walled flexible material and shaped to match the configuration of the contoured handle. The sterile disposable cover is fitted around the contoured handle in order to prevent the hands of surgical personnel from directly touching the handle when moving and/or focusing the lighting fixture during surgery. The cover includes a flange portion and an elongated, cylindrically-shaped, hollow grip portion. The grip portion has a plurality of elongated expandable channels formed therein, which facilitate fitting the cover over the contoured handle. The disposable cover may be used with contoured handles having different configurations. In an alternative embodiment, a length of tape, having pressure sensitive adhesive applied thereto, is attached to the disposable cover, and may be wrapped around the cover for the purpose of securing the cover to the handle. In another embodiment, a rigid or semi-rigid flange is attached to the upper surface of the cover flange. In yet another embodiment, one or more apertures may be provided in a surgical light handle for the purpose of venting trapped air from inside a cover, being fitted over the handle, into the interior of the hollow handle.

22 Claims, 5 Drawing Sheets

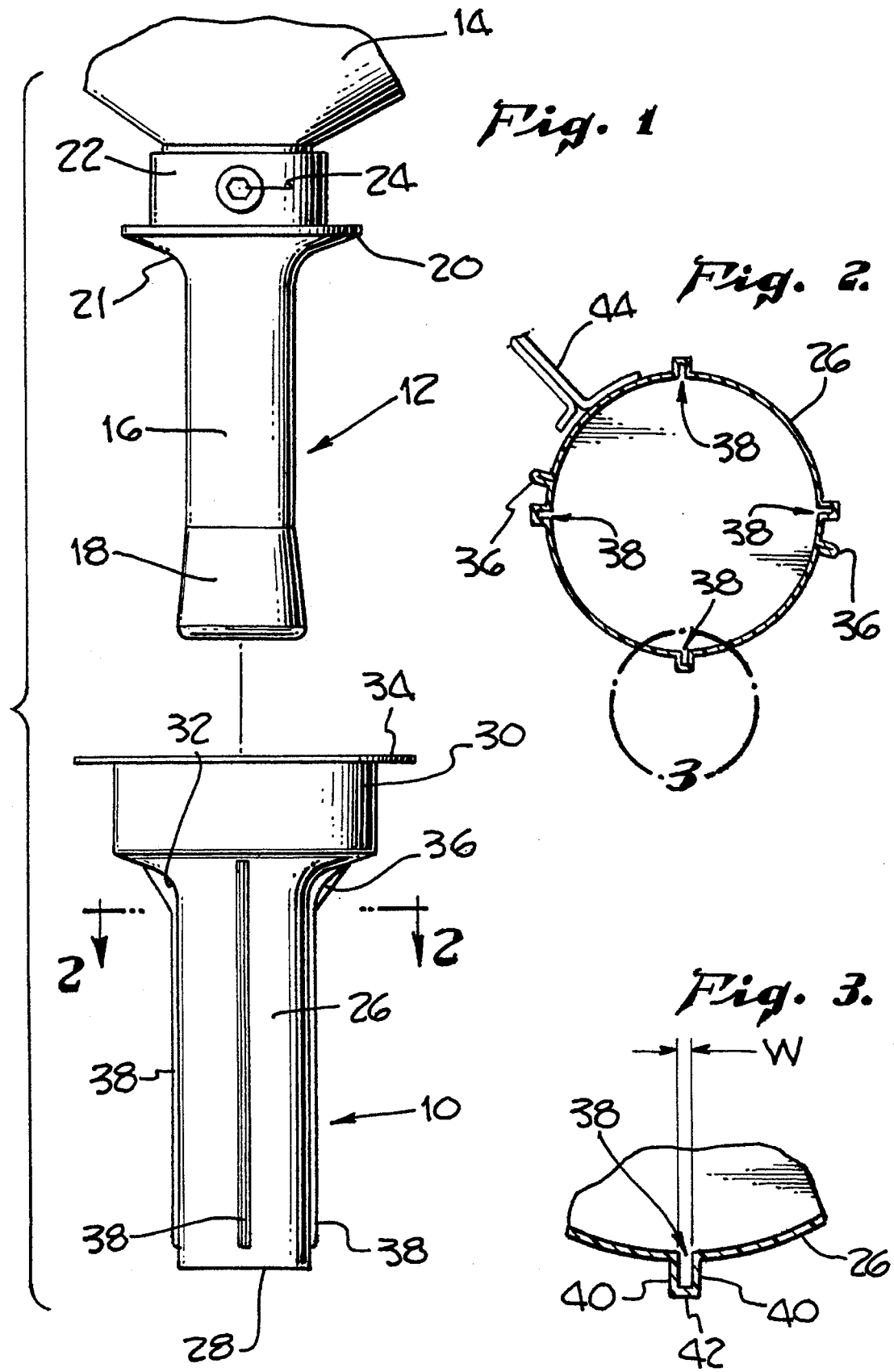

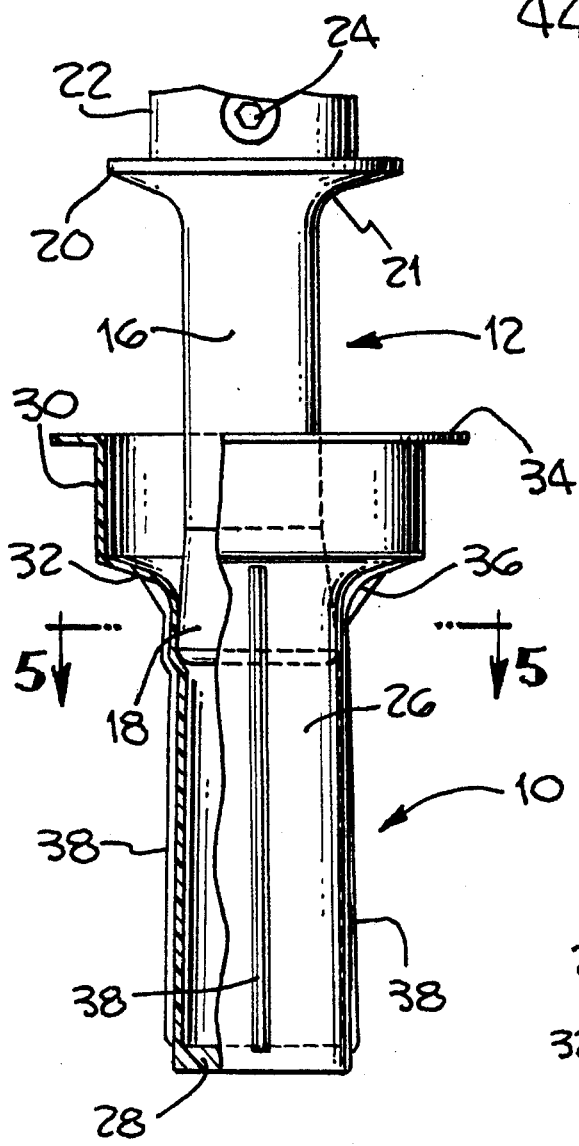
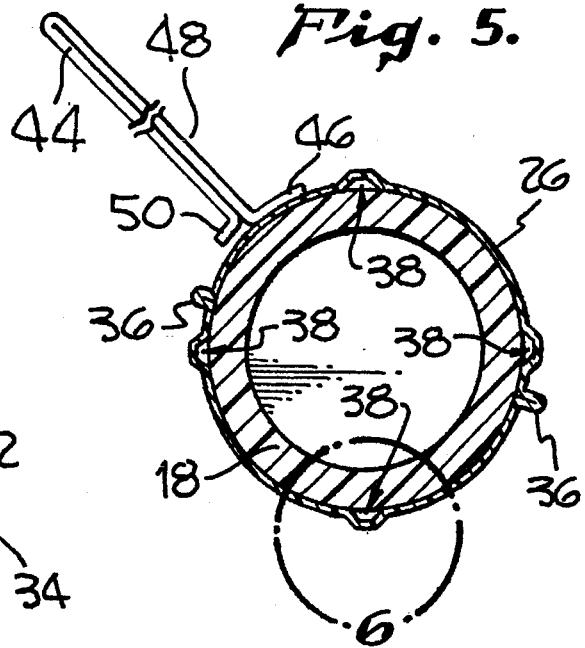
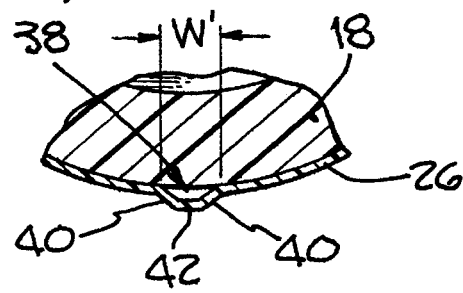
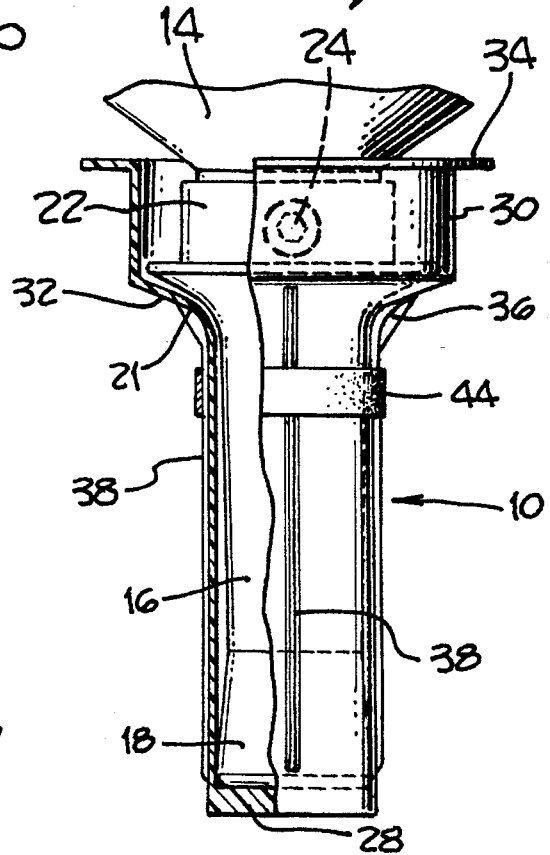

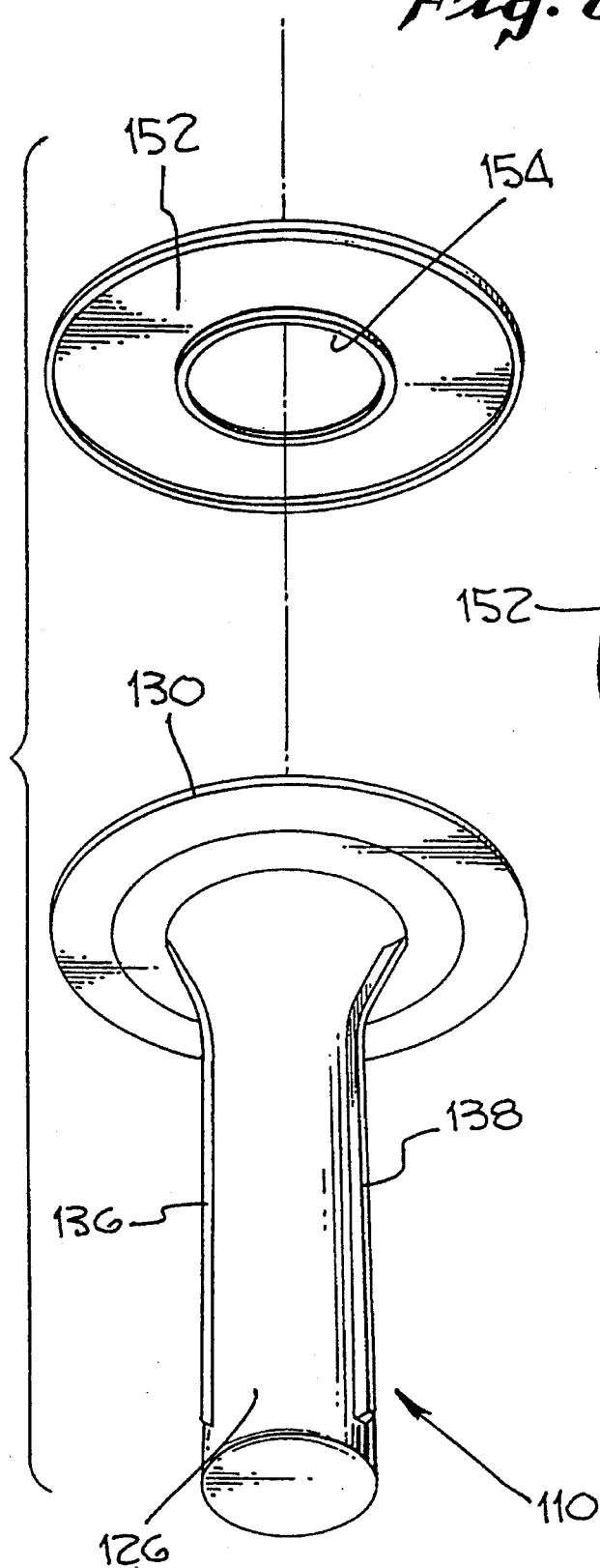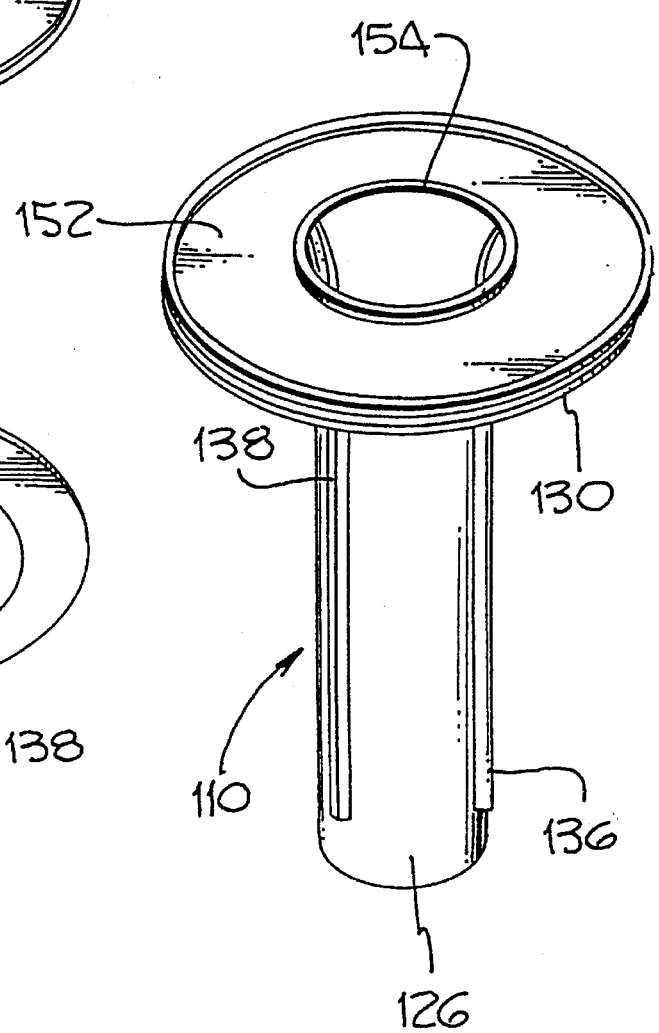

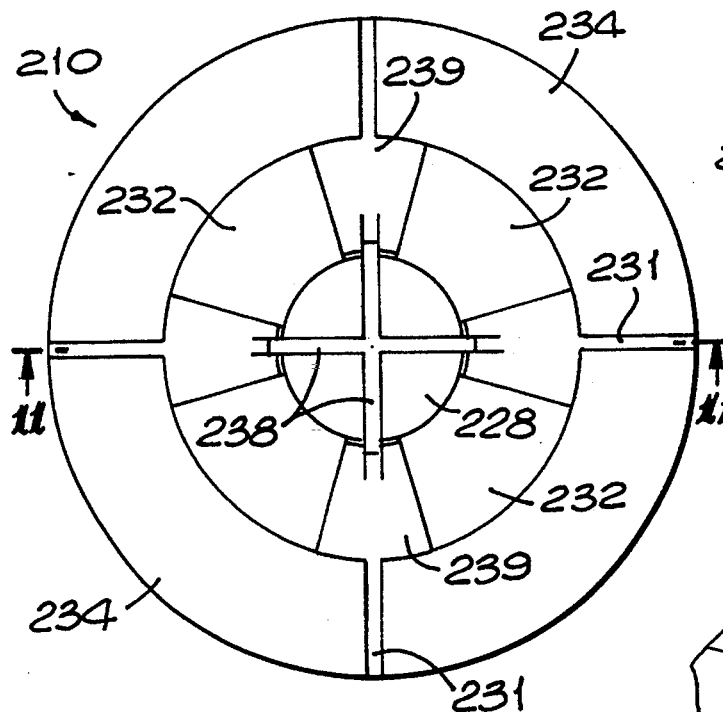
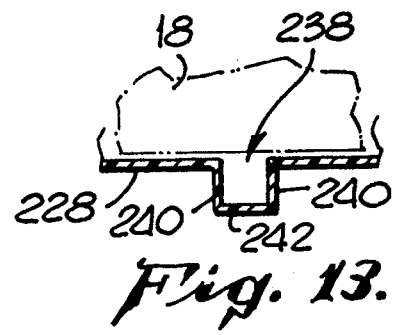
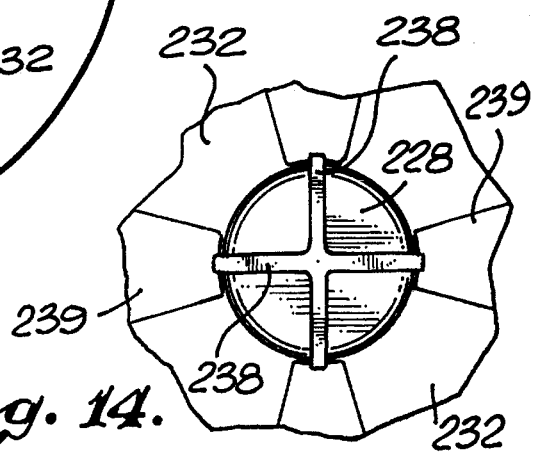
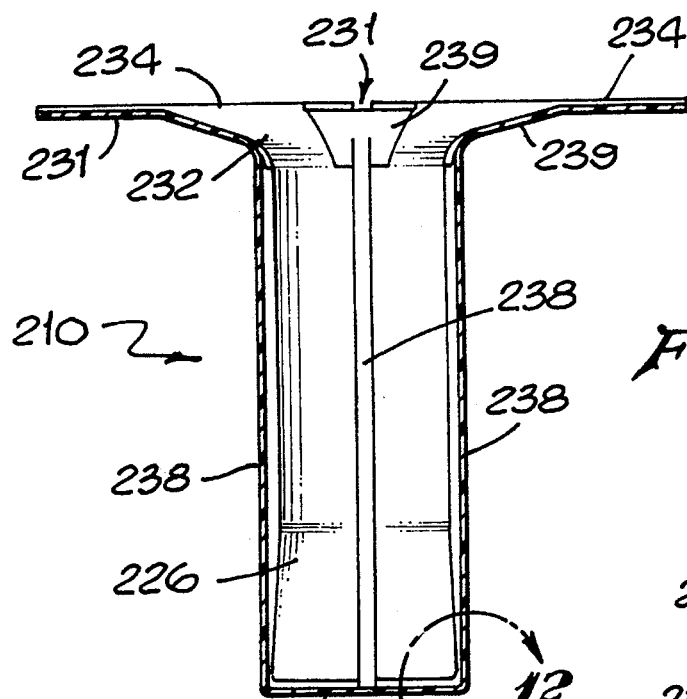
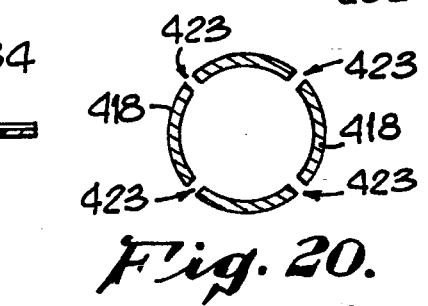
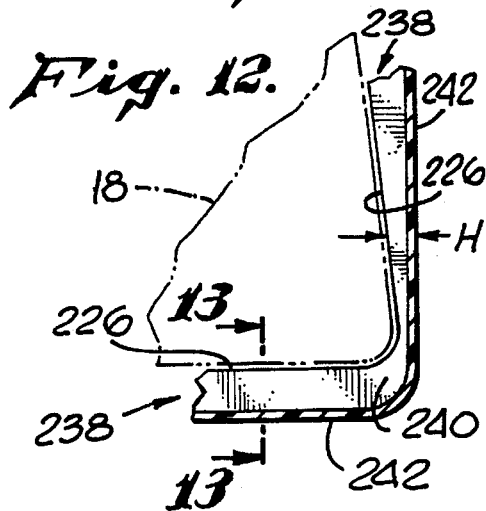

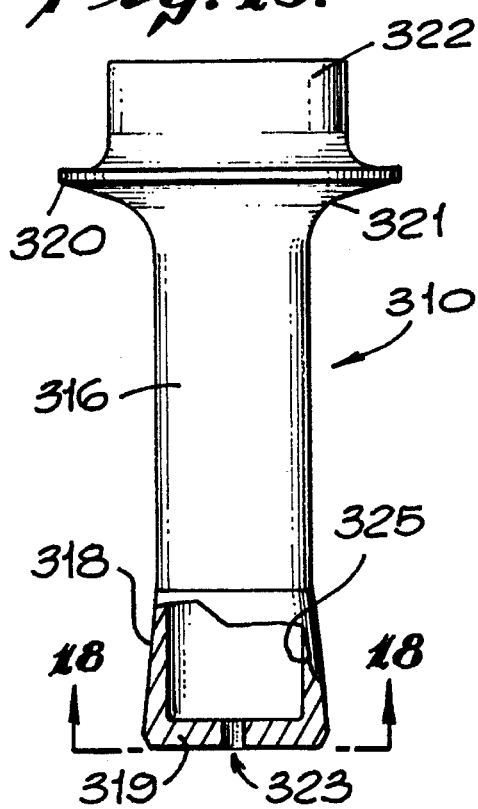
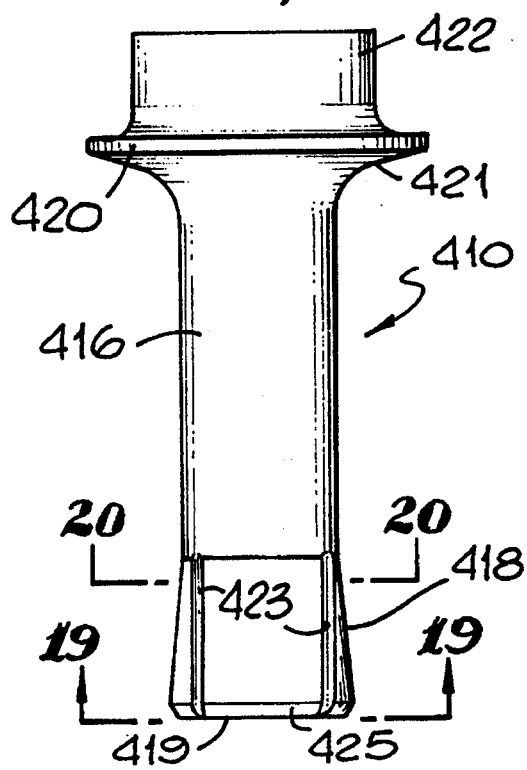
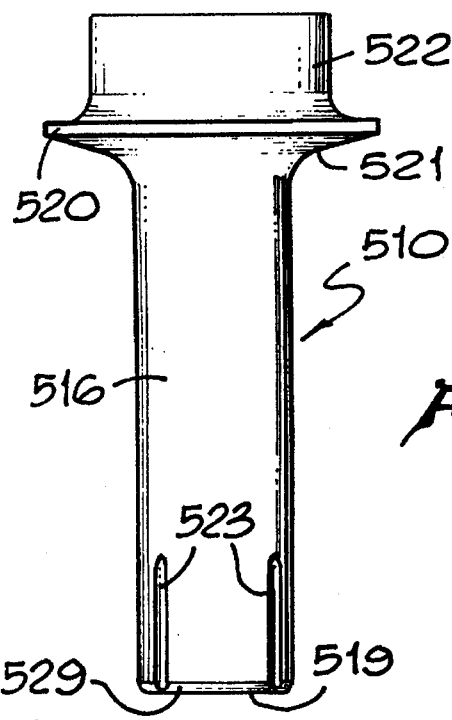
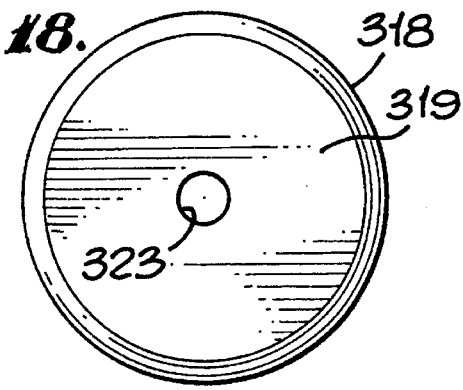
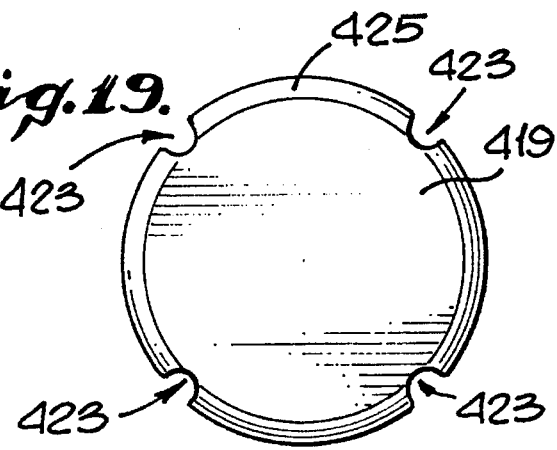

DISPOSABLE COVER FOR CONTOURED SURGICAL LIGHT HANDLE

CROSS-REFERENCE TO RELATED APPLICATION

This application is a continuation-in-part of application, Ser. No. 07/902,942, filed Jun. 23, 1992, abandoned, and entitled "DISPOSABLE COVER FOR CONTOURED SURGICAL LIGHT HANDLE."

BACKGROUND OF THE INVENTION

The present invention relates generally to hospital surgery room equipment, and more particularly to disposable covers used for handles of surgical room light fixtures.

Special lighting fixtures are used in operating rooms and surgical surroundings in order to provide adequate lighting for surgery. Surgical personnel are able to focus and adjust the position of such a lighting fixture during an operation by grasping a handle attached to the fixture, and moving the fixture to a desired position. In order to maintain a sterile operating environment, a disposable cover is provided that fits over the handle of the light fixture, thus preventing the hands of surgical personnel from directly touching the handle and adjacent portions of the light fixture.

One such disposable cover is disclosed in U.S. Pat. No. 4,605,124, issued to Sandel et al. on Aug. 12, 1986. This patent describes a disposable cover made from an integral thin-walled plastic or rubber-like material that fits over a handle of a light fixture. However, problems may be encountered in fitting such a disposable cover over a contoured handle having a non-uniform cross sectional configuration. Also, it may be difficult to fit the disposable cover securely to such a handle so that the cover will not come free of the handle during movement of a light fixture by surgical personnel.

SUMMARY OF THE INVENTION

It is an object of this invention to provide a disposable cover for a surgical light handle that is contoured.

It is another object of this invention to provide a disposable cover for different sizes of surgical light handles.

It is still another object of this invention to provide a disposable cover that may be securely fit to a surgical light handle.

It is still another object of this invention to provide a disposable cover for a surgical light handle that is economical to manufacture.

It is still another object of this invention to provide a surgical light handle adapted to vent air which is cover is being fitted over the handle.

It is still another object of this invention to provide a surgical light handle that is economical to manufacture.

These and other objects and advantages are attained by a disposable sterile cover for a contoured handle of a surgical lighting fixture, which is formed from a thin-walled flexible material and shaped to match the configuration of the contoured handle. The cover includes a flange portion and an elongated, cylindrically-shaped, hollow grip portion. The grip portion has a plurality of elongated expandable channels formed therein, which facilitate fitting the cover over the contoured handle.

The disposable cover may be used with contoured handles having different configurations. In an alternative embodiment a length of adhesive tape, having pressure sensitive adhesive applied thereto, may be attached to the disposable cover, and may be wrapped around the cover for the purpose of securing the cover to the handle.

In another embodiment, a rigid or semi-rigid flange is attached to the flange portion of the disposable cover. The cover flange has an aperture therein which facilitates fitting the cover assembly over a surgical light handle. This embodiment may be preferred where the surgical light handle or stud does not have a flange, or has a small flange.

In another alternative embodiment, a disposable cover is provided having elongated expandable channels which extend longitudinally down the grip portion of the cover, and across the bottom of the cover. As a result, air trapped between the cover and handle is vented out of the cover, when the cover is being fitted over the handle.

In yet another embodiment of the invention one or more apertures may be provided in a contoured handle for the purpose of venting trapped air from inside a cover into the interior of the hollow handle, while the cover is being fitted over the handle. Such apertures may also be used in a handle of uniform cross-section for the purpose of venting trapped air from inside a cover.

The various features of the present invention will be best understood together with further objects and advantages by reference to the following description of the preferred embodiments taken in conjunction with the accompanying drawings.

BRIEF DESCRIPTION OF THE DRAWINGS

FIG. 1 is an exploded elevational view of a contoured light handle shown attached to a surgical lighting fixture, and of a disposable cover of the present invention having a plurality of elongated, integral, expandable channels;

FIG. 2 is a cross-sectional view taken in the direction of arrows 2—2 shown in FIG. 1;

FIG. 3 is an enlarged, detailed cross-sectional view taken as indicated by numeral 3 in FIG. 2, showing one of the elongated expandable channels of the disposable cover of FIG. 1;

FIG. 4 is an elevational view showing the disposable cover being fit over the contoured handle;

FIG. 5 is a cross-sectional view taken in the direction of arrows 5—5 shown in FIG. 4, showing an alternative exemplary embodiment wherein adhesive tape is attached to the disposable cover, and illustrating how the elongated expandable channels expand allowing the contoured handle to be fit into a grip portion of the disposable cover;

FIG. 6 is an enlarged, detailed cross-sectional view taken as indicated by numeral 6 in FIG. 5, illustrating how one of the elongated channels expands or deforms;

FIG. 7 is an elevational view showing the disposable cover fit over the contoured handle and the adhesive tape wrapped around the cover and handle, securing the cover to the handle;

FIG. 8 is a perspective exploded view of another embodiment of the present invention, showing a rigid or semi-rigid flange to be attached to the flange and grip portion of an alternative form of the disposable cover;

FIG. 9 is a prospective view of the rigid or semirigid flange and cover of FIG. 8 shown in assembled relation;

FIG. 10 is a top plan view of another alternative embodiment of the disposable cover having elongated expandable channels which extend longitudinally down the grip portion of the cover, and across the end wall of the cover;

FIG. 11 is a cross-sectional view taken in the direction of arrows 11—11 shown in FIG. 10;

FIG. 12 is an enlarged, detailed cross-sectional, view taken as indicated by numeral 12 shown in FIG. 11, illustrating how one of the elongated channels extends across the end wall of the cover;

FIG. 13 is an enlarged, detailed cross-sectional view taken in the direction of arrows 13—13 shown in FIG. 12;

FIG. 14 is a partial bottom plan view of the disposable cover of FIG. 10;

FIG. 15 is an elevated view of a contoured surgical light handle of the present invention, having part of the lower portion of the handle broken away and shown in cross-section in order to show a vent aperture in the bottom or end wall of the handle;

FIG. 16 is an elevational view of another embodiment of the contoured surgical light handle, having a plurality of longitudinal slots in the lower portion of the handle;

FIG. 17 is an elevational view of another embodiment of a surgical light handle of the present invention, having a generally cylindrically-shaped handle grip with a plurality of longitudinal slots extending in an upward direction from the bottom of the grip;

FIG. 18 is a bottom plan view taken in the direction of arrows 18—18 shown in FIG. 15;

FIG. 19 is a bottom plan view taken in the direction of arrows 19—19 shown in FIG. 16; and FIG. 20 is a cross-sectional view taken in the direction of arrows 20—20 shown in FIG. 16.

DESCRIPTION OF THE PREFERRED EMBODIMENTS

The following specification taken in conjunction with the drawings sets forth the preferred embodiments of the present invention in such a manner that any person skilled in the art can make and use the invention. The embodiments of the invention disclosed herein are the best modes contemplated by the inventor for carrying out his invention in a commercial environment, although it should be understood that various modifications can be accomplished within the parameters of the present invention.

FIG. 1 shows a disposable cover 10 of the present invention which may be fit over a contoured handle 12 that is attached to a surgical lighting fixture 14. The disposable cover 10 is an improvement to the disposable cover disclosed in U.S. Pat. No. 4,605,124, issued to Sandel et al. on Aug. 12, 1986, the disclosure of which is hereby incorporated by reference thereto.

The contoured handle 12 shown in FIG. 1 has a handle grip which includes a generally cylindrically-shaped upper portion 16 and a generally frustoconically-shaped lower portion 18. An upper flange 20 having curved portion 21, is formed as an integral part of the handle 12, and a cylindrical head portion 22 extends upward from the flange 20. A fastener 24 is used to attach the handle 12 to the lighting fixture 14. However, the handle 12 may be connected to the fixture 14 by any desirable means such as threads, a snap ring, or the like.

It is important to note that the contoured handle 12 shown in FIG. 1 is only one example or configuration of a contoured handle 12 that may be used with the disposable cover 10 of the present invention. Any desirable contoured shape or configuration may be used for the handle 12, because the disposable cover 10 may be fabricated in accordance with the present invention to fit any such desirable contoured shape or configuration.

The disposable cover 10 of FIG. 1 is formed from a flexible thin-walled material to fit over the contoured handle 12. The cover 10 has a body which includes an elongated, generally cylindrically-shaped, hollow grip portion 26, which has a closed and generally flat end wall 28 (see FIG. 4), an upper, generally cylindrically-shaped, hollow body portion 30 at an open end thereof connected to grip portion 26 by curved interconnecting flared portion 32, and an annular upper flange 34 at the outer periphery of body portion 30.

The disposable cover 10 may be fabricated from any flexible or elastic sterilizable material such as plastic, synthetic rubber, silicone, latex, or any other material that will remain impervious even when exposed to any sterilizing agent. The material should preferably be thin and pliant. Additionally, the material preferably should have a low coefficient of friction surface on one side thereof for the inside surface of the disposable cover 10, and a higher coefficient of friction surface on the other side thereof for the outside surface of the cover, in order to allow easy assembly of the cover onto the handle 12 while allowing surgical personnel to grip the cover and handle. However, any material used in the industry for such disposable covers may be used for the disposable cover 10.

As shown in FIGS. 1 through 3, a plurality of reinforcing ribs 36 are formed in the disposable cover 10 at curved portion 32, and may extend longitudinally down the grip portion 26. Such reinforcing ribs 36 add rigidity to the disposable cover 10, and facilitate folding of the cover 10. In addition, a plurality of elongated expandable channels 38 are integrally formed in the disposable cover 10. The elongated expandable channels 38 are preferably formed in the flared, curved portion 32 and extend longitudinally down the grip portion 26. Any number of reinforcing ribs 36 and elongated expandable channels 38 may be used. The ribs and channels are preferably spaced equally and uniformly around the periphery of the disposable cover 10. Also, the ribs 36 and channels 38 may extend any distance down grip portion 26, although preferably all the way to the end. If desired, some of the reinforcing ribs 36 and expandable channels 38 may extend different distances down grip portion 26.

As best shown in FIG. 3, each elongated expandable channel 38 is formed in the outer periphery of the disposable cover 10 by two side walls 40 connected together by an end wall 42. As shown, walls 40 and 42 form generally rectangular-shaped channels 38 having a width W. However, the expandable channels 38 may have any desirable configuration or shape, such as semicircular, triangular, trapezoidal, or the like.

FIGS. 4 through 7 illustrate how the elongated expandable channels 38 facilitate fitting the disposable cover 10 over the contoured handle 12. While the handle 12 is attached to the lighting fixture 14, lower portion 18 of the handle 12 may be inserted into body portion 30 of the disposable cover 10, as shown in FIG. 4, and the cover 10 may then be pushed upward so that portion 18 enters grip portion 26 of the cover 10. If the bottom of portion 18 has a larger diameter than the internal diameter of the grip portion 26, then the expandable channels 38 will allow the internal diameter of grip portion 26 to increase in size when portion 18 is forced into portion 26, as discussed below, eventually allowing the cover 10 to be pushed upward until it fits around the handle 12 as shown in FIG. 7.

As the bottom of portion 18 enters grip portion 26 as shown in FIG. 4, the larger diameter of portion 18 "stretches" portion 26, or causes the internal diameter of portion 26 to increase in size, because the expandable channels 38 deform or "expand" into a generally trapezoidal shape as the width W of the channels 38 increases in size to width W. FIGS. 5 and 6 illustrate how the channels 38 deform under the pressure applied to the cover 10 by portion 18, resulting in an increased internal diameter for the grip portion 26, which allows the cover 10 to be pushed upward so that it fits around handle 12.

The disposable cover 10 is forced upward until curved portion 32 or the cover 10 bottoms or is pushed against curved portion 21 of the handle 12, and the portions 16 and 18 are inserted into grip portion 26. When in this position, the cover 10 will be held securely to the handle 12 because of the tight fit or the frictional contact between lower portion 18 of the handle 12 and the inside surface of grip portion 26.

In the case of a surgical light handle. 12 having a cylindrically-shaped flange that matches the cylindrical shape of cover body portion 30, the internal diameter of portion 30 is preferably made slightly smaller than the outside diameter of the handle flange. As a result, a snap fit will be provided between body portion 30 of the cover 10 and the handle flange, which helps to secure the cover 10 to the handle 12.

FIGS. 2, 5 and 7 illustrate how as an alternative exemplary embodiment of a means for securing the cover to the handle an adhesive tape 44 may be used to secure the disposable cover 10 to the surgical light handle 12. One end 46 of the tape 44 is attached to the cover 10 by any suitable means such as adhesive, sonic or heat welding, or the like. Pressure sensitive adhesive 48 is applied to one side of the tape 44 so that the tape 44 may be folded in half, and releasably secured to itself as shown in FIG. 5. However, any suitable adhesive may be used for the tape 44.

A tab 50 at the opposite end of the tape 44 may be grasped for the purpose of first pulling the two halves of the tape 44 apart, and then wrapping the tape 44 around the cover 10, after it is fitted around the handle 12, so that the adhesive 48 holds the tape 44 to the cover 10. As such, the cover 10 may be secured to the handle 12 by tightly wrapping the tape 44 around the cover 10. The cover 10 may be removed from the handle 12 by first grasping the tab 50 and unwrapping the tape 44 from around the cover 10, and then pulling or sliding the cover 10 free of the handle 12. A length of string or cord may be used instead of the tape 44, if desired.

As mentioned above, the disposable cover 10 may be used for any configuration or shape handle 12. For example, flange portion 30 of the cover 10 may have a conically-shaped configuration to match a corresponding flange configuration of a surgical light handle. As another example, the cylindrically-shaped grip portion 26 may be used with a larger size cylindrically-shaped handle. The channels 38 allow for expansion of the flared and grip portions of the cover body. As such, the disposable cover 10 may be used with different sizes of handles, and with handles having different configurations.

FIGS. 8 and 9 show another embodiment of the present invention having a rigid or semi-rigid disc or flange 152 attached to the grip portion 126 of the disposable cover 110. The rigid flange 152 may be attached to the upper surface of cover flange 130 by adhesive, sonic or heat welding, or any suitable fastening means. The cover 110 which may be used by itself or in association with disc 152 has reinforcing ribs 136 and expandable channels 138 as disclosed hereinbefore.

Flange 152 has an aperture 154 which allows the cover 110 to be fit around a surgical light handle as described above. In order to allow cover 110 to fit around the surgical light handle, the diameter of aperture 154 may be longer or smaller than the diameter of flange 20, and the diameter of flange 152 may be larger or smaller than the diameter of flange 20. However, because a rigid or semirigid flange 152 is provided with the disposable cover 110, the cover 110 may be used with a surgical light handle or stud that does not have a handle associated flange. Alternatively, the cover 110 and flange 152 may be used with handle 12 shown in FIG. 1 which has a small handle flange portion 20, thus providing a larger hand protecting flange. The disc or flange 152 may be made out of any suitable material such as plastic, cardboard, or the like.

Difficulties may be encountered while fitting a disposable cover over a surgical light handle due to air pressure building up between the cover and handle as the cover is pushed or fit over the handle. If the air pressure is too high, the thin-walled flexible material used for the cover may break or rupture. The following preferred embodiments of the present invention provide means for venting air trapped between the cover and handle, while the cover is pushed over the handle.

FIGS. 10 through 14 show another embodiment of the disposable cover 210 of the present invention. The disposable cover 210 has a flexible, thin-walled, generally cylindrically-shaped grip portion 226. At the open end of the disposable cover 210, a cover flange 234 is integrally interconnected to grip portion 226 by a curved, flared portion 232. The cover 210 may be made out of any flexible or elastic sterilizable material, as discussed above. Reinforcing ribs (not shown) may be used for the cover 210, if desired, such as reinforcing ribs 36 described above.

A plurality of elongated expandable channels 238, such as channels 38 discussed below, are integrally formed in the disposable cover 210. The expandable channels 238 are preferably integrally formed in the flared, curved portion 232, and extend longitudinally down the grip portion 226 and across a bottom or generally flat end wall 238 of the grip portion 226. Each of the expandable channels 238 has side walls 240 connected together by an end wall 242, as shown in FIG. 13, and is adapted to expand like the expandable channels 38 in order to allow the cover 210 to be fit over the contoured light handle 12. Any number of expandable channels 238 may be used. However, each expandable channel 23.8 on one side of the grip portion 226 has a corresponding expandable channel 238 on the opposite side of the grip portion, so that the opposite channels 238 are in communication with each other, or are interconnected by the same channel 238 crossing the bottom 228 of the cover 210, as shown in FIG. 14.

Wider channels 239 are integrally formed in the flared, curved portion 232. Each of the channels 239 has side walls connected by an end wall (not shown). As shown in FIGS. 10 and 11, each of the channels 239 is integrally connected to, or in communication with, the top end of a corresponding one of the expandable channels 238. The channels 239 are shown having a tapered shape, but any desirable shape or configuration may be used. Additional channels 231 are integrally formed in the cover flange 234. Each channel 231 has side walls connected by an end wall (not shown). As shown, each of the channels 231 is integrally connected to, in communication with, or extending into a corresponding one of the wider channels 239.

Referring to FIG. 12, the grip portion 226 may be shaped to better fit or conform to the shape of the lower portion 18 of the contoured handle 12 so that the height H of the expandable channels 238 varies near the bottom 228 of the cover 210. However, any desirable shape or configuration may be used for the grip portion 226.

The embodiment of the disposable cover 210 facilitates fitting the cover over a contoured handle 12, because the expandable channels 238 are used as means for venting air trapped between the cover 238 and handle 12. In other words, as the cover 210 is pushed over the handle 12, air pressure increases near the bottom 228 of the cover. This causes the air trapped near the bottom 228 of the cover 210 to enter the expandable channels 238 crossing the bottom 228 of the cover, and to pass in an upward direction through the expandable channels, and longitudinally along the length of the cover. The air reaches the top ends of the expandable channels 238, enters the wide channels 239, and then enters the channels 231 in the cover flange 234. Finally, the air exits the channels 231, and is vented or forced out of the cover 210. The channels 231 and 239 provide a pathway or means for venting the trapped air out of the cover 210, even though the cover is pushed up against the flange 20 and curved portion 21 of the handle 12.

The disposable cover 210 of FIGS. 10 through 14 may also be used with a surgical light handle having a handle grip with a uniform cross-section.

FIGS. 15 and 18 show a contoured surgical light handle 310 of the present invention having a vent aperture 323 in a bottom or end wall 319 of the handle. The vent aperture 323 is used as means for venting air trapped between a cover and the handle 310, while the cover is being pushed over the handle.

The contoured handle 310 has a handle grip which includes a generally cylindrically-shaped upper portion 316 and a generally frustoconically-shaped lower portion 318. As shown, the handle 310 is hollow, and may have an internal diameter 325. The handle 310 may be used with or without a handle flange 320 and curved portion 321. A fastener 24 may be used to attach head portion 322 of the handle 310 to a lighting fixture 14 (see FIG. 1). However, any suitable means may be used for fastening the handle 310 to the lighting fixture.

As a cover is fit over the handle 310, air trapped between the cover and handle 310 will be forced or vented through the vent aperture 323, and into the interior of the hollow handle. Thus, the vent aperture 323 is used as means for venting trapped air out of the cover. The aperture 323 may have any desirable shape or configuration, and more than one aperture 323 may be used.

Another embodiment of a contoured surgical light handle 410 of the present invention is shown in FIGS. 16, 19 and 20. A plurality of elongated or longitudinal slots or apertures 423 are used in a lower portion 418 of the handle 410 as means for venting trapped air out of a cover and into the interior of the hollow handle. The elongated slots 423 extend into an annular edge 425 adjacent a bottom 419 of lower portion 418 in order to facilitate passing the trapped air into the slots 423. If desired, the slots 423 may extend into the bottom 419 of the handle 410. Any desirable number of elongated slots or apertures 423 may be used, and the apertures 423 may have any desirable shape. Preferably, four slots 423 are used and positioned around the handle 410, as shown in FIG. 19.

FIG. 17 shows another embodiment of a surgical light handle 510 of the present invention having a generally cylindrically-shaped handle grip 516 of uniform cross-section. A plurality of elongated or longitudinal slots or apertures 523 extend in an upward direction from a bottom 519 of the handle 510. The elongated slots 523 are used as means for venting trapped air out of a cover and into the interior of the hollow handle 510. Any number of elongated slots or apertures 523 may be used, and the apertures 523 may extend any distance up the handle grip 516. In addition, the apertures 523 may have any desirable shape. The slots 523 are show extending into an annular edge 525 adjacent the bottom 519 of the handle 510. However, the elongated slots 523 may extend into the bottom 519 of the handle 510, if desired.

Alternatively, the embodiments of the handles 410 and 510 may have vent apertures like aperture 323 in the bottoms 419 and 519, respectively, of the handles. Also, elongated slots such as slots 423 and 523 may be used for handle 310, if desired. Any type of slot or aperture may be used in the handle of the present invention as means for venting trapped air out of a cover and into the interior of the hollow handle. It is intended that such vent means not be limited to the exact configuration of slots and apertures shown in FIGS. 15 through 20.

The within specification has described the preferred embodiments of the present invention. However, persons of ordinary skill in the art are capable of numerous modifications once taught these principles. Accordingly, it will be understood by those skilled in the art that changes in form and details may be made to the above-described embodiments without departing from the spirit and scope of the invention.

What is claimed is:

1. A disposable cover for a handle of a surgical room light fixture which is normally positioned above an operating table and handled by surgical personnel during operations, said light fixture handle including a handle grip extending from a handle flange, said cover comprising:

a sterile, disposable, thin-walled, substantially impervious, flexible body including a hollow elongated grip portion, a closed longitudinal end and a cover flange, said elongated grip portion defining an outer circumferential surface and a longitudinal length and being adapted to be fitted over said light fixture handle; and one or more elongated thin-walled expandable channels formed in said thin-walled flexible body and adapted to facilitate fitting said cover over said light fixture handle, said expandable channels extending radially outwardly of said outer circumference and along substantially more than half of the longitudinal length of said grip portion and defining an outer surface substantially parallel to said outer circumferential surface of said grip portion along substantially more than half of the longitudinal length of said grip portion.

2. The disposable cover of claim 1 wherein said thin-walled flexible body further includes a flared portion interconnecting said cover flange and said grip portion and said one or more channels extend into said flared portion to facilitate expansion of said flared portion as it is fitted over said handle.

3. The disposable cover of claim 2 wherein said light fixture handle is a contoured handle.

4. The disposable cover of claim 3 wherein each of said one or more of said expandable channels is adapted to deform when said cover is fitted over said light fixture handle in order to facilitate fitting said cover over said handle.

5. The disposable cover of claim 1 further comprising a rigid or semi-rigid disc secured to said cover flange, said disc being larger than said handle flange of said light fixture handle, and having an aperture therein.

6. As disposable handle cover for a handle of a surgical room light fixture as claimed in claim 1, wherein said one or more elongated thin-walled expandable channels comprises:

a first elongated thin-walled expandable channel having two circumferentially spaced portions extending along said grip portion and connected to one another by a lower portion extending along said closed longitudinal end; and a second elongated thin-walled expandable channel having two circumferentially spaced portions extending along said grip portion and connected to one another by a lower portion extending along said closed longitudinal end, said lower portion of said first elongated thin-walled expandable channel crossing said lower portion of said second elongated thin-walled expandable channel.

7. As disposable handle cover for a handle of a surgical room light fixture as claimed in claim 1, wherein at least one of said elongated thin-walled expandable channels extends substantially to said closed longitudinal end.

8. As disposable handle cover for a handle of a surgical room light fixture as claimed in claim 1, wherein at least one of said elongated thin-walled expandable channels extends to said closed longitudinal end.

9. A disposable cover for a handle of a surgical room light fixture which is normally positioned above an operating table and handled by surgical personnel during operations, said light fixture handle including a handle grip extending from a handle flange, said cover comprising:

a sterile, disposable, thin-walled, impervious, flexible body including a hollow elongated grip portion, a cover flange, said cover adapted to be fitted over said light fixture handle;

one or more elongated thin-walled expandable channels formed in said thin-walled flexible body and adapted to facilitate fitting said cover over said light fixture handle, said expandable channels extending substantially along a longitudinal length of said grip portion; and a length of tape attached to said cover, said tape having a pressure sensitive adhesive applied thereto, and being adapted to be wrapped around said cover in order to secure said cover to said handle.

10. A disposable cover for a handle of a surgical room light fixture which is normally positioned above an operating table and handled by surgical personnel during operations, said light fixture handle having a configuration including a handle grip extending from a handle flange, said cover comprising:

a sterile, disposable, thin-walled, substantially impervious, flexible body including a hollow elongated grip portion defining an outer circumferential surface and a longitudinal length, a cover flange and a body portion integral with said grip portion at an open end thereof, said thin-walled flexible body having a configuration adapted to facilitate fitting said cover over said light fixture handle; and one or more elongated thin-walled expandable channels formed in substantially more than half of the longitudinal length of said grip portion and adapted to facilitate fitting said cover over said light fixture handle, at least one of said channels including first and second side walls and an end wall, each of said side walls being moveable between a non-use position, wherein said side walls are substantially parallel to one another, and a use position, when the cover is mounted on a handle, wherein said side walls are non-parallel, said end wall being substantially parallel to said outer circumferential surface of said grip portion along substantially more than half of the longitudinal length of said grip portion.

11. The disposable cover of claim 10 wherein said thin-walled flexible body further includes a flared portion interconnecting said body portion and said grip portion and said one or more channels extending into said flared portion to facilitate expansion of said flared portion as it is fitted over said handle.

12. The disposable cover of claim 10 further comprising a rigid or semi-rigid disc mounted to said flange portion of said cover, said disc being larger than said handle flange of said light fixture handle and having an aperture therein.

13. A disposable cover for a handle of a surgical room light fixture which is normally positioned above an operating table and handled by surgical personnel during operations, said light fixture handle having a configuration including a handle grip extending from a handle flange, said cover comprising:

a sterile, disposable, thin-walled, impervious, flexible body including a hollow elongated grip portion, a cover flange and a body portion integral with said grip portion at an open end thereof, said thin-walled flexible body having a configuration adapted to facilitate fitting said cover over said light fixture handle;

one or more elongated thin-walled expandable channels formed in said thin-walled flexible body and adapted to facilitate fitting said cover over said light fixture handle, said expandable channels extending substantially along a longitudinal length of said grip portion; and a length of tape attached to said cover, said tape having a pressure sensitive adhesive applied thereto, and being adapted to be wrapped around said cover in order to secure said cover to said handle.

14. A disposable cover for a handle of a surgical room light fixture which is normally positioned above an operating table, said cover comprising:

a sterile, disposable, thin-walled, impervious, flexible body including a hollow elongated grip portion and a cover flange;

a length of tape attached to said cover, said tape having a pressure sensitive adhesive applied thereto, and being adapted to be wrapped around said cover in order to secure said cover to said light fixture handle; and one or more thin-walled elongated expandable channels formed in said thin-walled flexible body and adapted to facilitate fitting said cover over said light fixture handle, said expandable channels extending substantially along a longitudinal length of said grip portion.

15. The disposable cover of claim 14 wherein each said expandable channels is adapted to deform when said cover is fitted over said light fixture handle in order to facilitate fitting said cover over said light fixture handle.

16. The disposable cover of claim 15 wherein said thin-walled flexible body further includes a flared hollow portion interconnecting said grip portion and said cover flange and at least one of said one or more channels extends into said flared hollow portion.

17. The disposable cover of claim 14 further comprising a rigid or semi-rigid disc mounted to said cover flange, said disc having an aperture therein to facilitate fitting said cover over said light fixture handle.

18. A disposable cover for a handle of a surgical room light fixture which is normally positioned above an operating table and handled by surgical personnel during operations, said light fixture handle including a handle grip extending from a handle flange, said cover comprising:

- a sterile, disposable, thin-walled, impervious, flexible body including a hollow elongated grip portion having a bottom and a cover flange, said cover adapted to be fitted over said light fixture handle; and
- one or more elongated thin-walled expandable channels formed in said thin-walled flexible body and adapted to facilitate fitting said cover over said light fixture handle, said expandable channels extending along a longitudinal length of said grip portion and across said bottom of said grip portion.

19. The disposable cover of claim 18 wherein said thin-walled flexible body further includes a flared portion interconnecting said cover flange and said grip portion.

20. The disposable cover of claim 19 wherein said flared portion has one or more channels formed therein, said one or more expandable channels being integrally connected to said one or more channels in said flared portion.

21. The disposable cover of claim 20 wherein said cover flange has one or more channels formed therein, said one or more channels in said flared portion being integrally connected to said one or more channels in said cover flange.

22. A disposable cover for a handle of a surgical room light fixture which is normally positioned above an operating table and handled by surgical personnel during operations, said light fixture handle having a configuration including a handle grip extending from a handle flange, said cover comprising:

- a sterile, disposable, thin-walled, substantially impervious, flexible body including a hollow elongated grip portion having a bottom and a cover flange, said cover adapted to be fitted over said light fixture handle; and
- an elongate channel, formed in said flexible body and having two circumferentially spaced channel portions extending along said grip portion and connected to one another by a lower channel portion extending along the bottom of said grip portion, for venting air trapped between said cover and said handle out of said cover during fitting of said cover over said handle.

* * * * *